United States Patent [19]

Avila

[11] Plant 5,143

[45] Nov. 22, 1983

[54] *ILEX AQUIFOLIUM* SELECTION

[75] Inventor: Rosendo Avila, Azusa, Calif.

[73] Assignee: Monrovia Nursery Company, Azusa, Calif.

[21] Appl. No.: 356,334

[22] Filed: Mar. 9, 1982

[51] Int. Cl.[3] ..... A01H 5/12

[52] U.S. Cl. ..... Plt./65

[58] Field of Search ..... Plt./65

*Primary Examiner*—Robert E. Bagwill

[57] ABSTRACT

This invention relates to a new and distinct selection of *Ilex aquifolium* shrub (popularly known as English holly) a member of the Aquifoliaceae family referred to as *Ilex aquifolium* 'Monvila'. A sport selection characterized from the plant it was discovered on by its variegated leaf with yellow margins. Our selection differs from *Ilex aquifolium* 'Argenteo-marginata', a plant with similar foliage color pattern by our new selection having (1) a more compact growth habit; (2) smaller leaves with less numbers of spines and (3) producing strictly male flowers.

2 Drawing Figures

DISCOVERY

This new and distinct *Ilex aquifolium* 'Monvila' was discovered as a variegated sport in a bed of a sexually propagated *Ilex aquifolium* 'Little Bull' (also known as *Ilex aquifolium* 'Teufel's Little Bull'). The parent plant, *Ilex aquifolium* 'Little Bull' is not patented or trademarked and originated as a selection of *Ilex aquifolium* 'Angustifolia'. This new variegated sport was discovered in April 1977 by Rosendo Avila at Monrovia Nursery Company, 18331 East Foothill Boulevard, Azusa, Calif.

The plant to date is known to exist only within the boundaries of Monrovia Nursery and has not been offered for sale or described in any publication.

REPRODUCTION

*Ilex aquifolium* 'Monvila' has been strictly asexually reproduced at Monrovia Nursery by vegetative cuttings to preserve the genetic attributes which make it different from the parent. The potential loss of these genetic attributes in sexual reproduction prohibits propagation by seed. Seed progeny of *Ilex aquifolium* 'Monvila' has not been observed.

CHARACTERISTICS

This new selection differs from the parent it was found on by its leaf color pattern. Our new selection has a variegated leaf pattern of glossy green in the center and yellow bordering the margins. The parent plant has dark green leaves with no yellow color.

This new selection resembles somewhat *Ilex aquifolium* 'Argenteo-marginata' in color. However, our selection differs in obvious characteristics such as having a much more compact habit and tighter growth. (See illustration FIG. 1).

Also the leaves are much smaller in our new selection, approximately half the size in width and length and have less pairs of spines, generally 5 to 7 pairs, whereas *Ilex aquifolium* 'Argenteo-marginata' has generally 10 to 12 pairs of spines. (See illustration FIG. 2)

Our new selection has the attributes of its parent, *Ilex aquifolium* 'Little Bull' and even improves on them with its showy yellow green foliage. Our selection also improves on a holly with similar foliage color, *Ilex aquifolium* 'Argenteo-marginata', with our selection having a more compact growth habit, smaller leaves, less spines and having only male flowers (a pollenizer). The combination of these characteristics make for a more desirable and superior plant for ornamental and landscape use.

DESCRIPTION

Below is a detailed description of the new variety, all color terminology is from the British Horticultural Colour Charts.

Overall size and habit: At five years this plant will have grown four to five feet in height and width. Habit is an evergreen shrub.

Foliage:

- *Length.*—1 to 1½ inches.
- *Width.*—½ to ¾ inches.
- *Shape.*—Narrowly-elliptic to oblong-elliptic. Tip: Cuspidate Base: attenuate to obtuse.
- *Color.*—Upper margins: Sulphur Yellow 1. Upper center: Ivy Green 0001060.
- *Pattern.*—Leaf center green irregularly blending into yellow margins.
- *Margins.*—Spinescent, 5 to 7 parts of spines plus tip spine; reflexed and sometimes undulate.
- *Texture.*—Coriaceous.
- *Arrangement.*—Alternate.
- *Pubescence.*—Glabrous.
- *Petioles.*—3/16 to ¼ inch in length.

Flower:

- *Size.*—¼ to 5/16 inch in diameter, clustered in leaf axils.
- *Petal.*—Number: generally 4 sometimes 5. Shape: rounded, widely-obovate.
- *Sex.*—Dioecious, male.
- *Pistil.*—None.
- *Stamens.*—Generally 4 sometimes 5.

Fruit: None.

I claim:

1. *Ilex aquifolium* 'Monvila' is a new and distinct selection as substantially shown and described herein, a superior selection characterized by a combination of notable characteristics of variegated foliage, compact habit, small foliage and having strictly male flowers.

* * * * *

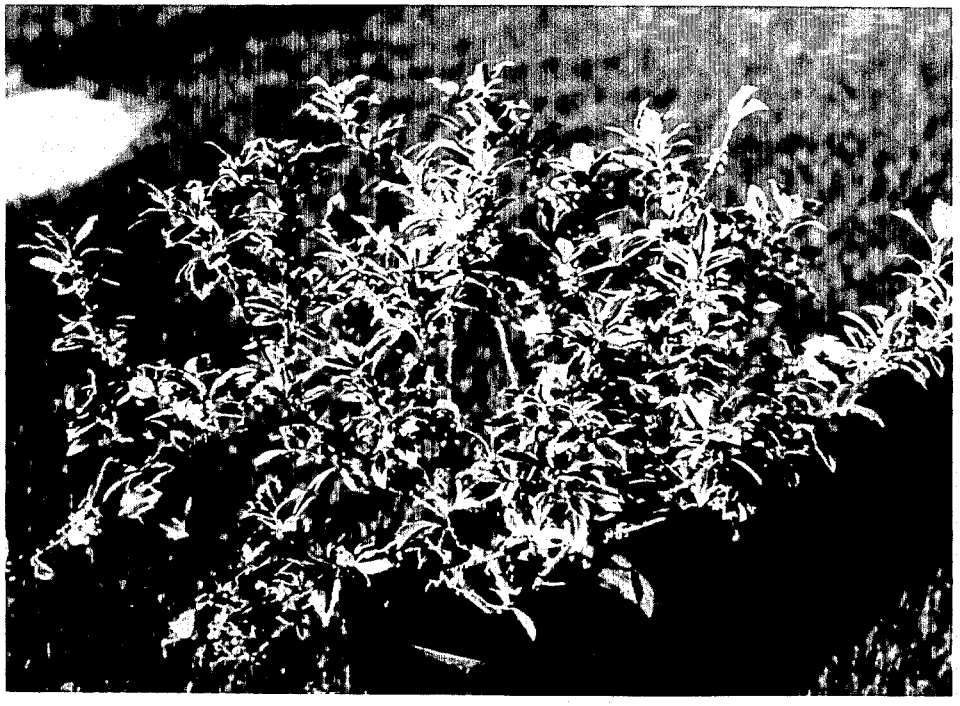
FIG. 1 SELECTION
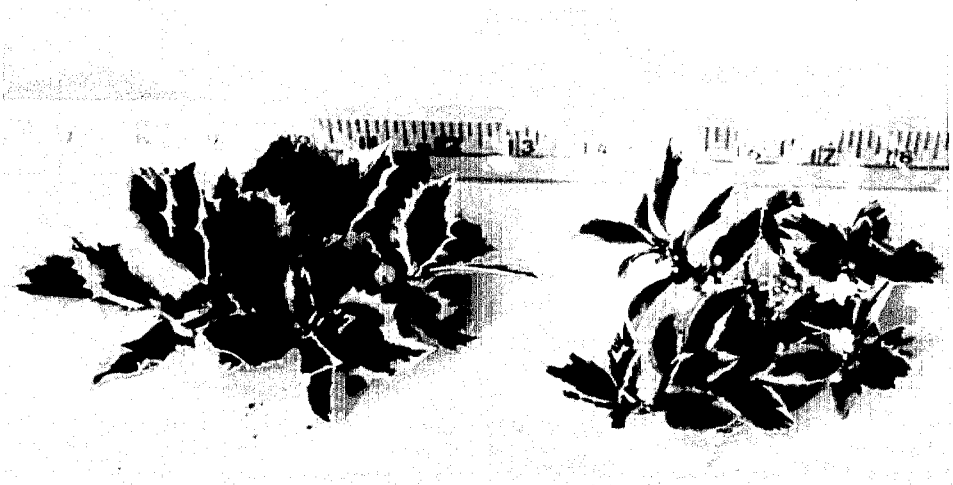
PRIOR ART FIG. 2 SELECTION